(12) United States Patent
Betz

(10) Patent No.: US 10,569,303 B2
(45) Date of Patent: Feb. 25, 2020

(54) ULTRASONIC TRANSDUCER, AND METHOD FOR PRODUCING AN ULTRASONIC TRANSDUCER

(71) Applicant: SYSTEC CONTROLS MESS—UND REGELTECHNIK GMBH, Puchheim (DE)

(72) Inventor: Oliver Betz, Groebenzell (DE)

(73) Assignee: Systec Controls Mess- ung Regeltechnik GmbH, Puchheim (DE)

( * ) Notice: Subject to any disclaimer, the term of this patent is extended or adjusted under 35 U.S.C. 154(b) by 573 days.

(21) Appl. No.: 14/426,217

(22) PCT Filed: Sep. 3, 2013

(86) PCT No.: PCT/EP2013/068203
§ 371 (c)(1),
(2) Date: Mar. 5, 2015

(87) PCT Pub. No.: WO2014/037354
PCT Pub. Date: Mar. 13, 2014

(65) Prior Publication Data
US 2015/0209828 A1    Jul. 30, 2015

(30) Foreign Application Priority Data
Sep. 5, 2012   (DE) .......................... 10 2012 108 254

(51) Int. Cl.
*B06B 1/06* (2006.01)
*H01L 41/053* (2006.01)
(Continued)

(52) U.S. Cl.
CPC .......... *B06B 1/0644* (2013.01); *B06B 1/0207* (2013.01); *B32B 37/0076* (2013.01);
(Continued)

(58) Field of Classification Search
CPC ....... B06B 1/06; B06B 1/0603; B06B 1/0644; B06B 1/0648; B06B 1/0651; B06B 1/0655
(Continued)

(56) References Cited

U.S. PATENT DOCUMENTS 4,705,981 A    11/1987 Inoue et al.
4,746,831 A    5/1988 Ichino
(Continued)

FOREIGN PATENT DOCUMENTS

AT             6059 U1    3/2003
EP          1237148 A2    9/2002
(Continued)

*Primary Examiner* — Derek J Rosenau
(74) *Attorney, Agent, or Firm* — Laurence A. Greenberg; Werner H. Stemer; Ralph E. Locher

(57) ABSTRACT

An ultrasonic transducer includes a housing and a piezo element. The piezo element is inserted into a cavity of the housing and the housing has a covering which covers the cavity. A spring element is disposed between the covering and the piezo element. The spring element applies a spring force onto the piezo element and the covering has a plurality of conductor tracks or paths which contact through or plate through the covering. An assembly for insertion into the housing and a method for assembling an ultrasonic transducer are also provided.

7 Claims, 2 Drawing Sheets

(51) Int. Cl.
*B06B 1/02* (2006.01)
*B32B 37/00* (2006.01)
*B32B 37/06* (2006.01)
*B32B 37/14* (2006.01)
*B32B 37/18* (2006.01)
*B32B 38/00* (2006.01)
*H04R 31/00* (2006.01)

(52) U.S. Cl.
CPC ............ *B32B 37/06* (2013.01); *B32B 37/142* (2013.01); *B32B 37/18* (2013.01); *B32B 38/0008* (2013.01); *H01L 41/053* (2013.01); *H01L 41/0536* (2013.01); *H04R 31/00* (2013.01); *B32B 2307/20* (2013.01); *B32B 2307/202* (2013.01); *B32B 2310/028* (2013.01); *B32B 2457/00* (2013.01); *Y10T 29/42* (2015.01)

(58) Field of Classification Search
USPC .................................................. 310/322, 334
See application file for complete search history.

(56) References Cited

U.S. PATENT DOCUMENTS

| | | | |
|---|---|---|---|
| 5,339,292 A * | 8/1994 | Brown | .................. B06B 1/0681 310/334 |
| 7,087,264 B2 | 8/2006 | Suzuki et al. | |
| 7,307,373 B2 * | 12/2007 | Straub, Jr. | ................ G01F 1/662 310/334 |
| 7,737,609 B2 | 6/2010 | Murata et al. | |
| 8,904,881 B2 | 12/2014 | Sonnenberg et al. | |
| 2005/0225204 A1 * | 10/2005 | Beck | ..................... B06B 1/0618 310/322 |
| 2007/0209440 A1 | 9/2007 | Dockendorff et al. | |
| 2013/0327155 A1 | 12/2013 | Drachmann | |

FOREIGN PATENT DOCUMENTS

| | | |
|---|---|---|
| EP | 1840530 A2 | 10/2007 |
| EP | 2076062 A1 | 7/2009 |
| JP | H11325992 A | 11/1999 |
| JP | 2011015265 A | 1/2011 |
| WO | 9706761 A1 | 2/1997 |
| WO | 9910110 A1 | 3/1999 |
| WO | 2011141167 A2 | 11/2011 |
| WO | 2012113401 A1 | 8/2012 |

* cited by examiner

ULTRASONIC TRANSDUCER, AND METHOD FOR PRODUCING AN ULTRASONIC TRANSDUCER

BACKGROUND OF THE INVENTION

Field of the Invention

The invention relates to an ultrasonic transducer wherein the ultrasonic transducer comprises a housing and a piezo element which is inserted into a cavity in the housing. The cavity is covered by a covering means which is arranged in the housing. A spring is arranged between the covering element and the piezo element, said spring applying a spring force to the piezo element. The invention further relates to a method for assembling an ultrasonic transducer, and to an assembly for installation into the housing of an ultrasonic transducer.

Ultrasonic transducers of this kind are used for a large number of measurements. The ultrasound used for measuring purposes is generated by a piezoelectric element being made to oscillate due to a change in voltage. The ultrasound which is generated in this way is received, directly or after reflection at an interface, by a receiver. The receiver converts the ultrasonic signals acting on it back into a change in voltage. The ultrasonic transducer of the kind cited in the introductory part is likewise suitable as a receiver, so that it can be used both as a generator and also as a receiver of ultrasonic signals. Ultrasonic transducers of this kind are used, for example, as pressure sensors or filling level sensors. They have proven to be particularly effective as sensors for flowmeters.

The flow rate of a medium flowing through the line can be determined without a great deal of expenditure using an ultrasonic flowmeter. Various methods can be used for measurement purposes, the propagation time difference measurement of the ultrasonic signals which are emitted by the ultrasonic transducer being a method which is frequently used. The mass throughflow rate or the volumetric throughflow rate in the line can then be calculated with a high degree of precision from the measurement results obtained.

A particular advantage of ultrasonic flowmeters is that they do not necessarily have to be installed in the line which is to be measured, but rather can also be used as so-called clamp-on measuring devices. In many cases, it is entirely adequate for the ultrasonic transducers to be fastened to the outside of the line for measurement purposes. Non-invasive measurement provides the advantage that an opening in the line, which opening is required for insertion of the sensor, can be dispensed with. Problems in respect of leaktightness do not occur at all here. A further advantage is that clamp-on measuring devices do not generate any interference in the pipe cross section and there is therefore no risk of the measurement result being corrupted by a local changes in flow which is caused by the sensor.

In addition to stationary use, the clamp-on flowmeters, which can be fitted without a great deal of expenditure, are also suitable for mobile use in changing measurement locations. For this purpose, it is only necessary for said clamp-on flowmeter to be calibrated to the respective line cross section and the material which is used for the wall of the pipe.

An ultrasonic transducer substantially comprises a piezo element, that is inserted into a cavity which is formed in the housing of the ultrasonic transducer. The piezo element, which is inserted into the cavity, is pressed from the inside against this outer wall of the housing by spring force. With respect to the rest of the housing, the cavity is closed by a covering means, said cavity usually being covered by a simple plate.

A covering means of this kind is required since, for safety reasons, the interior of the ultrasonic transducer is, in most cases, provided with a potting encapsulation after the piezo element is fitted. The plate which covers the cavity is intended to prevent the liquid potting compound from entering the cavity and disabling the effect of the spring element when the ultrasonic transducer is potted. In addition, the plate can be used as an abutment for the spring which presses the piezo element against the housing inner wall.

Although an ultrasonic transducer has only a few components, assembly of said parts is relatively complicated. Before the housing can be potted, the piezo element first has to be contact-connected to the outside. This is achieved by means of cables which are routed in the housing and connect the piezo element to the connections of the ultrasonic transducer which are provided on the rear face of the housing. An opening or a cable channel is provided in the plate which covers the cavity, the cables having to be threaded through said opening or cable channel in order to route said cables out of the cavity. That end of the cable connection which is remote from the piezo element is soldered to the external interface of the ultrasonic transducer, that is to say the connection of said ultrasonic transducer, on the housing. In addition, impedance matching is almost always required. Said impedance matching is achieved by the interconnection of an inductance.

After cabling is complete, the cavity has to be sealed off from the remainder of the housing. A plate which is situated only on the cavity would not completely close said cavity; it would not be possible to reliably prevent potting compound entering the cavity in this way. In order to be able to ensure the leaktightness of the cavity in as simple a manner as possible, the plate is adhesively bonded to the housing. To this end, the plate is positioned in the desired position over the cavity and is fixed there, for example using a splint. Said plate is then provided with an adhesive along the housing, said adhesive, after it has cured, connecting the plate to the housing and sealing off the cavity. The opening present in the plate is likewise adhesively bonded and thus sealed off with respect to the cabling which is threaded through said opening.

BRIEF SUMMARY OF THE INVENTION

The object of the present application is to provide an ultrasonic transducer, manufacture of said ultrasonic transducer being simpler in comparison to the ultrasonic transducers of the kind described in the introductory part. An assembly which can be prefabricated and with which an ultrasonic transducer can be assembled quickly and simply is also proposed. In addition, a method which simplifies assembly of an ultrasonic transducer is proposed.

The respective objects are achieved by the following: An ultrasonic transducer, which comprises a housing, a piezo element inserted into a cavity in the housing, a covering disposed in the housing and covering the cavity, a spring element disposed between the covering element and the piezo element and applying a spring force to the piezo element, and the covering having a plurality of conductor tracks which plate-through or contact through the covering; An assembly for insertion into a housing of an ultrasonic transducer, which comprises a covering for closing a cavity provided in the ultrasonic transducer for receiving a piezo element, the covering having electrical conductors which contact through or plate-through the covering, a piezo element connected to the electrical conductors, and a spring element disposed between the piezo element and the covering; and A method for assembling an ultrasonic transducer, which comprises forming a cavity in a housing of the ultrasonic transducer, inserting a piezo element into the cavity, closing the cavity using a covering after inserting the said piezo element, and connecting the piezo element to conductor tracks which contact through or plate-through the covering. Advantageous refinements can be found in the associated dependent claims.

In the refinement of the ultrasonic transducer according to the invention, said ultrasonic transducer has a plurality of conductor tracks, or electrical conductors, which plate-through the covering means. One of the conductor tracks in each case connects a contact area, which is arranged on that face of the covering means which faces the piezo element, to a contact area on the opposite face of the covering means. The covering means is almost in the form of a kind of printed circuit board, or printed circuit, as a result. The electrical conductors are accordingly integrated into the covering means, that is to say are integrally formed with the covering means. The piezo element is connected to the covering means on that face which faces the cavity, and the external interface of the ultrasonic transducer, which interface is arranged on the housing, is connected to that face which is remote from the cavity. As a result, it is not only possible to dispense with the process of threading cables through the opening in the covering means, as has been required to date for the purpose of making contact with the piezo element, but the opening itself is no longer required either. As a result, it is not necessary to close and seal off said opening before potting the ultrasonic transducer, as is otherwise required, either. It is now only necessary to insert the covering means into the ultrasonic transducer in order to close the cavity.

The cables which connect the piezo element to the external interface therefore no longer have to be routed through an opening, instead two separate cables respectively make contact with the contact points which are provided for them on a face of the covering means. A first cable connects the piezo element to the covering means, the second cable connects the covering means to the external interface of the ultrasonic transducer. The first cable and the second cable are again connected to one another by the covering means. The conductor tracks which are integrated into the covering means are therefore part of an electrical connection which contact-connects the piezo element to the external interfaces of the ultrasonic transducer, which external interfaces are arranged on the housing.

One very particular advantage of this solution is that it allows elements of the ultrasonic transducer according to the invention to be fitted together in advance as an assembly before being installed into the transducer housing. The proposed assembly, which can be prefabricated, has a covering means for closing a cavity in the ultrasonic transducer, which cavity is provided for receiving a piezo element, wherein the covering means comprises electrical conductors according to the invention which plate-through the covering means, and wherein the assembly has a piezo element which is connected to the electrical conductors, and wherein a spring element is arranged between the piezo element and the covering element. This assembly is preferably already assembled outside the ultrasonic transducer, since, in this way, access is easily possible from all sides. In particular, the piezo element and the covering element are easily accessible in this way and can be connected to one another without obstruction. It is then only necessary for the prefabricated assembly to be further connected to the external interface of the ultrasonic transducer. The contact points of the covering means, which contact points are provided for this purpose, are themselves still easily accessible after the assembly is positioned. Assembly of the ultrasonic transducer is considerably simplified as a result.

At least the contact points of the conductor tracks, which contact points are arranged on that face of the covering means which is averted from the piezo element, are preferably in the form of solder areas. Designing the contact points as solder areas, so-called solder pads, additionally simplifies the process of making contact with the cables and therefore further accelerate the assembly of the ultrasonic transducer.

In a particularly preferred embodiment, the covering means comprises at least one electrical or electronic component. This allows a component of this kind to be provided in the connection of piezo element and external interface of the ultrasonic transducer without said component first having to be interconnected into the connection in a complicated manner. The component can already be connected to the conductor track of the covering means before fitting, and therefore no additional connections apart from the contact-making connections of the first cable and of the second cable are required during assembly of the ultrasonic transducer.

The covering means preferably comprises at least one inductance for impedance matching of the piezo element. Impedance matching is required at regular intervals, as described. If the printed circuit is already fitted with the inductance which is inserted into the conductor tracks, the discretionary wiring of the coil which otherwise has to be carried out during the contact-making process can be dispensed with.

It is particularly advantageous when the covering means comprises an active electronic component, for example a sensor identifier which reached the piezo element which is used in the ultrasonic transducer.

In one particularly preferred embodiment, the ultrasonic transducer has a covering means which is held in the converter housing by means of a bayonet fitting. An essential basic concept of this aspect of the invention is to design the connection between the covering means and the transducer housing to be self-supporting. The plug-and-turn connection proposed for this purpose allows an interlocking connection between the two parts in a manner which is known per se.

The covering means is fixed by the bayonet fitting being closed in the desired position which covers the cavity. In this case, the spring element which is arranged between the covering means and the piezo element additionally assists sealing-off of the cavity. The spring force which is exerted on the piezo element by the spring element presses the covering means in the opposite direction against the housing-end part of the bayonet fitting and seals off the cavity. The interlocking connection which is established in this way allows the additional working step of adhesively bonding the covering means to the housing which was previously required to be dispensed with. As a result, the covering means therefore no longer has to be held in position either, as was previously necessary for adhesive-bonding purposes. Assembly of the ultrasonic transducer is significantly simplified in this way.

The specific refinement of the bayonet principle, that is to say how the covering means is inserted into the housing and is moved, by means of turning between the covering means and the transducer housing, into a position in which it is held on the housing in an interlocking manner, can be matched to the respective conditions without particular difficulty.

The bayonet fitting preferably comprises a thread. The thread allows the housing-end part and the covering means-end part of the bayonet fitting to be guided towards one another by turning until they are in full contact. The two closure parts are therefore pressed against one another during turning along the thread, as a result of which sealing-off of the cavity is further improved.

The piezo element and the covering means are connected to one another during assembly. The piezo element is, as it were, prestressed by the spring element. The assembly is then fastened to the housing of the ultrasonic transducer by means of the bayonet fitting, wherein the piezo element is pressed against the inner face of the housing by the spring element. After the bayonet fitting is closed, the piezo element is in the intended position, and the cavity is closed in a leaktight manner at the same time. Before subsequent potting, it is only necessary for the contacts on that side of the printed circuit which is averted from the cavity to be connected to the electrical or electronic interfaces of the ultrasonic transducer. The piezo element is then connected to the connections of the ultrasonic transducer, which connections are arranged on the housing, by means of the conductor tracks which plate-through the covering means.

As an alternative fastening method, the covering means is welded to the housing, in particular by ultrasonic welding. This manner of fastening by way of a cohesive connection seals off the cavity particularly well.

Quite fundamentally, the fastening method for the covering means can also be considered separately from the design of the covering means with conductor tracks which plate-through said covering means. The described advantages of the fastening methods using a bayonet fitting or ultrasonic welding can also be realized independently of the design of the covering means as a printed circuit. The inventive features of the ultrasonic transducer and the assembly are therefore not necessarily required for this purpose.

BRIEF DESCRIPTION OF THE SEVERAL VIEWS OF THE DRAWING

Two particularly preferred embodiments of the invention will be described in greater detail below with reference to two drawings, in which.

DESCRIPTION OF THE INVENTION

Figure 1:
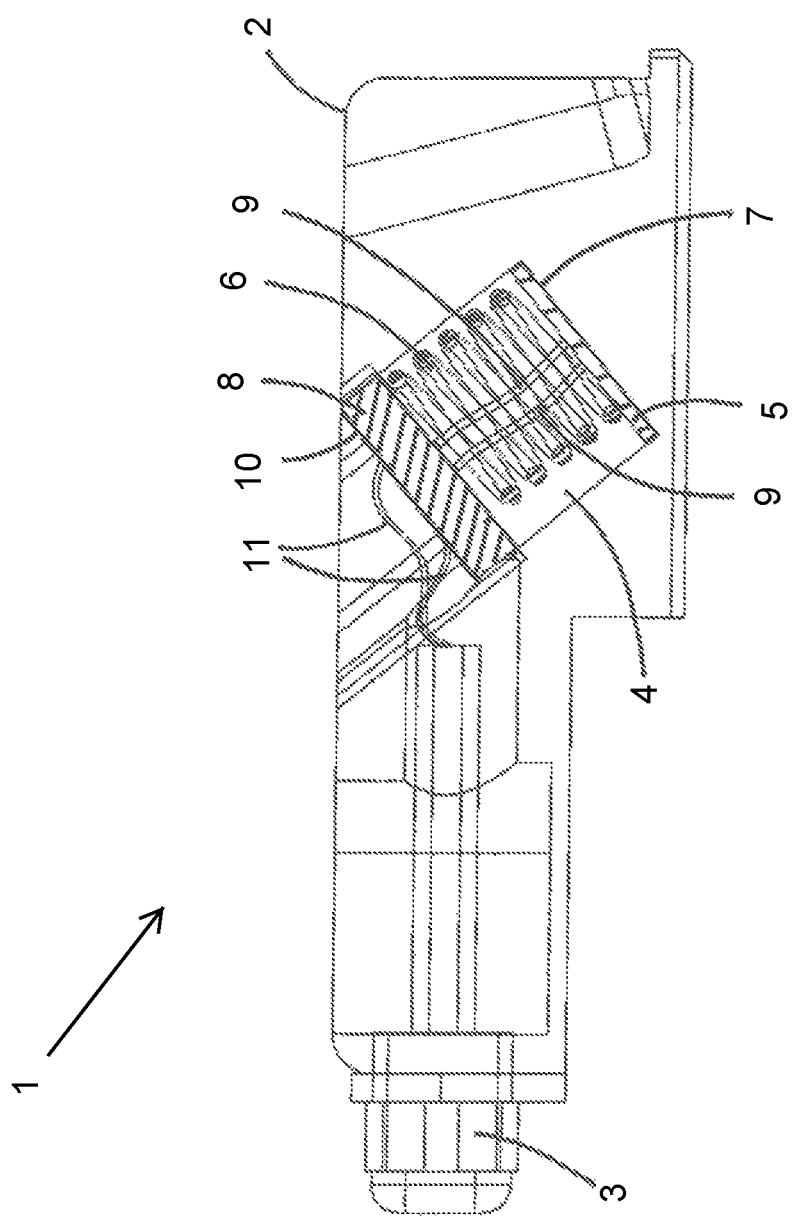
FIG. 1: is a schematic illustration of an assembled ultrasonic transducer with a covering plate in the form of a printed circuit.

The ultrasonic transducer 1 shown in FIG. 1 has a housing 2 and a connection 3, which is fastened to the housing 2, for a cable connection, not shown here, for connection of the ultrasonic transducer 1 to a control device. A piezo element 5 is arranged in a cavity 4 in the housing 2 which is shown partially open. A spring 6 acts on the piezo element 5, said spring pressing said piezo element against a wall 7 of the cavity 4. That end of the spring 6 which is remote from the piezo element 5 bears against a covering means 8 which covers the cavity 4. The covering means is fastened to the housing 2 by a holding means, not shown here, and seals off the cavity from the ingress of potting compound.

The covering means 8 has conductor tracks which plate-through said covering means, and is therefore in the form of a printed circuit. Conductor tracks are connected to the piezo element 5 by means of cables 9 on that face of the covering means 8 which faces the cavity 4. In this case, the cables 9 run in the form of a spring 6 which is in the form of a helical spring. The covering means 8, the spring 6 and the piezo element 5, which is connected to the covering means 8 by means of the cables 9, form an assembly. The assembly can be prefabricated outside the housing 2 and be inserted into the transducer housing 2 after said assembly is assembled.

On account of the conductor tracks, the covering means 8 does not require an opening for cables which make contact with the piezo element 5 on the outside. Said covering means is of continuous design. That area 10 of said covering means which is averted from the cavity 4 therefore does not have any apertures through which the potting compound can enter the cavity 4. Solder pads by means of which the cables 11 are connected to the conductor tracks which plate-through the piezo element 5 are provided in the area 10. The cables 11 run through the housing 2 as far as the connection 3 by means of which the piezo element 5 can be connected to a control device.

Figure 2:
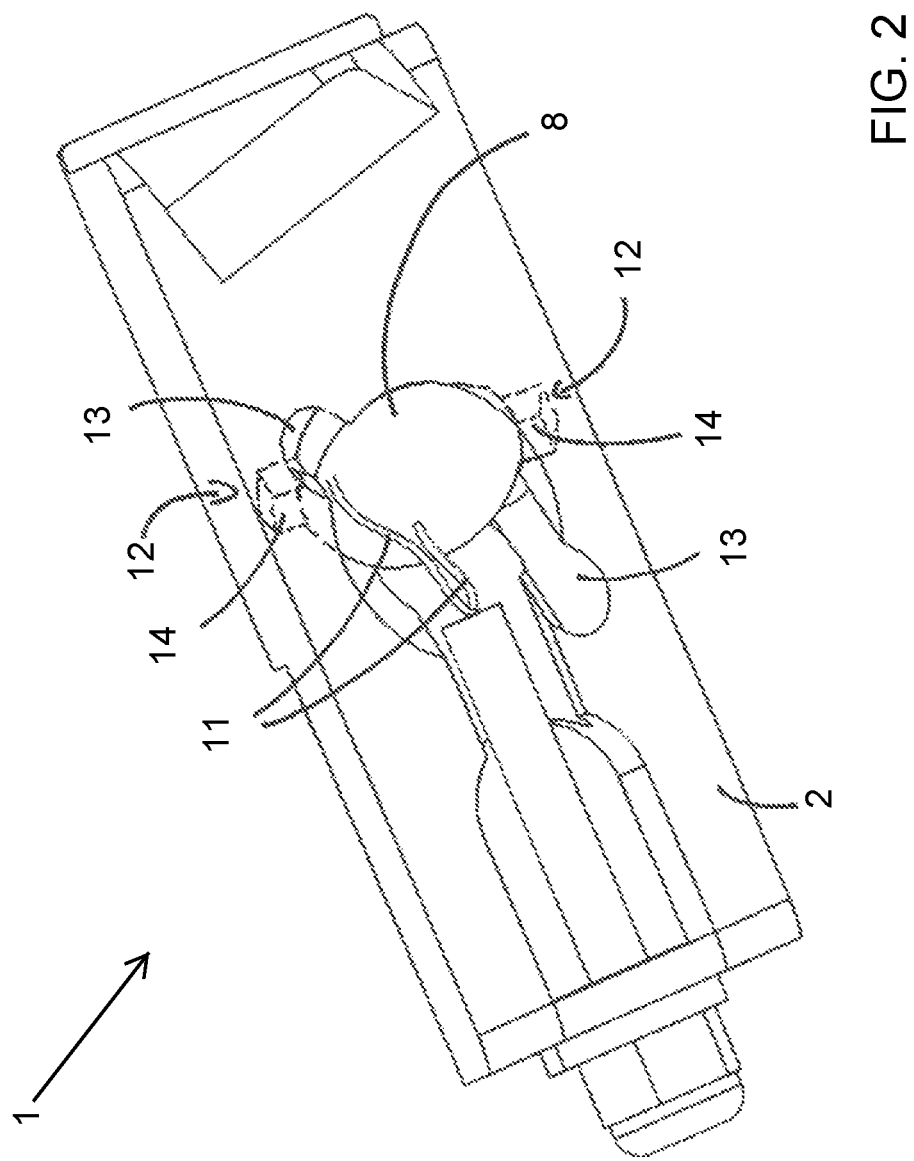
FIG. 2: is a schematic illustration of an ultrasonic transducer having a covering plate in the form of a printed circuit which is held in the housing by means of a bayonet fitting.

FIG. 2 shows a further partially open ultrasonic transducer 1 in which the holding means of the covering means 8 is a bayonet fitting 12. The circular covering means 8 has two projecting pegs on its circumference, said pegs being inserted into slots 13 which are arranged on a likewise circular opening in the housing 2 above the cavity 4 in a manner offset 180 degrees in relation to one another. The slots 13 are adjoined by a side slot which is formed transversely to said slots and in which the pegs are inserted by turning the covering means 8. The pegs 14 which are received in the transverse slot and illustrated using dashed lines here undercut the longitudinal slot 13 and in this way secure the covering means 8 in its position above the cavity 4, so that said covering means can seal off the cavity from potting compound which is introduced into the housing. The cables 11 are provided with an adequate degree of play, so that they do not impede turning of the covering means 8.

The invention claimed is:

1. An ultrasonic transducer, comprising:
    a housing having a cavity and a remainder of said housing;
    a piezo element inserted into said cavity in said housing;
    a covering disposed in said housing and covering said cavity, said covering including at least one inductance for impedance matching of said piezo element, said covering having a plurality of electrical conductor tracks plated-through and integrally formed with said covering, said covering including at least one electrical or electronic component, and said covering sealing off said cavity from said remainder of said housing; and
    a spring element disposed between said covering and said piezo element, said spring element applying a spring force to said piezo element.

2. The ultrasonic transducer according to claim 1, wherein said covering has a surface facing away from said piezo element, and said plated-through conductor tracks have contact points formed as solder areas disposed on said surface of said covering facing away from said piezo element.

3. The ultrasonic transducer according to claim 1, wherein said covering includes a sensor identifier.

4. The ultrasonic transducer according to claim 1, which further comprises a bayonet fitting holding said covering in said housing.

5. The ultrasonic transducer according to claim 4, wherein said bayonet fitting has a thread.

6. The ultrasonic transducer according to claim 1, wherein said covering is welded to said housing.

7. An assembly for insertion into a housing of an ultrasonic transducer having a cavity in the housing and a remainder of the housing, the assembly comprising:
- a covering for closing the cavity being formed in the ultrasonic transducer for receiving a piezo element, said covering including at least one inductance for impedance matching of said piezo element, said covering including electrical conductors plated-through and integrally formed with said covering, said covering including at least one electrical or electronic component, and said covering sealing off the cavity from the remainder of the housing;
- the piezo element connected to said electrical conductors; and
- a spring element disposed between said piezo element and said covering.

* * * * *